United States Patent [19]

Galambos et al.

[11] 4,438,132

[45] Mar. 20, 1984

[54] 4-OXO-PGI₂ COMPOUNDS, THEIR USE IN INHIBITION OF THROMBII AND THEIR PRODUCTION

[75] Inventors: Gaza Galambos; Vilmos Simonidesz; Istvan Szekely; Jozsef Ivanics; Krisztina Kekesi; Gabor Kovacs; Istvan Stadler; Peter Körmoczy; Karoly Horvath, all of Budapest, Hungary

[73] Assignee: CHINOIN Gyogyszer es Vegyeszeti Termekek Gyara Rt., Hungary

[21] Appl. No.: 368,013

[22] Filed: Apr. 13, 1982

[30] Foreign Application Priority Data

Apr. 14, 1981 [HU] Hungary ............................ 2251/966

[51] Int. Cl.³ ................. A61K 31/557; C07D 307/935
[52] U.S. Cl. .................................... 424/285; 549/465; 549/214
[58] Field of Search ................ 549/465; 542/421, 423, 542/426, 429; 424/285

[56] References Cited

U.S. PATENT DOCUMENTS 4,126,744 11/1968 Ayer .................................. 549/465

Primary Examiner—Henry R. Jiles
Assistant Examiner—Bernard Dentz
Attorney, Agent, or Firm—Karl F. Ross; Herbert Dubno

[57] ABSTRACT

The invention relates to a process for the preparation of novel 4-oxo-PGI₂ derivatives of formula I

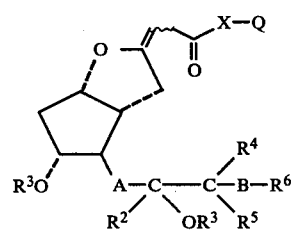

where
(a) compounds of formula III

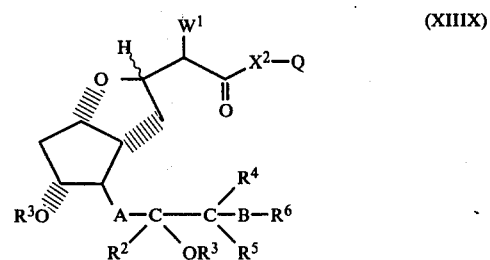

are oxidized, then the obtained 5-substituted-4-oxo-PGI₁ derivatives of general formula II

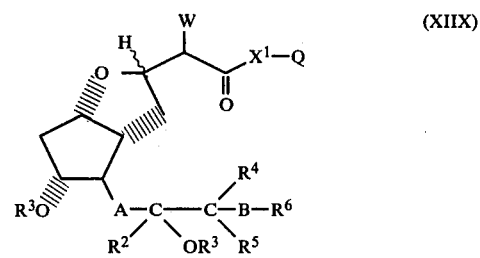

are eliminated by the splitting off of the W-H-molecule, or
(b) the compounds of formula IV

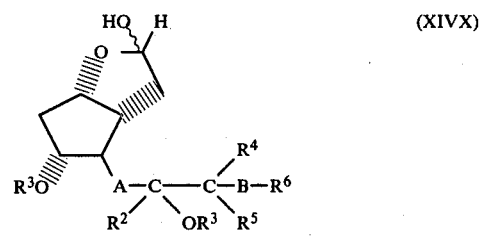

are reacted in a solvent in the presence of a catalyst with compounds of general formula V

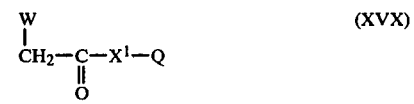

then the obtained compounds of formula I are transformed if desired by saponification, hydrolysis, salt formation, insertion of a protection group to another compound which belongs to the compounds of formula I, too.

The pharmaceutical products of the invention can be used for the treatment of circulatory diseases, they inhibit the aggregation of blood plaques, dilate the bronchi and inhibit the secretion of gastric acid.

39 Claims, No Drawings

4-OXO-PGI₂ COMPOUNDS, THEIR USE IN INHIBITION OF THROMBII AND THEIR PRODUCTION

The invention relates to a process for the preparation of optically active or racemic 4-oxo-PGI₂ of the formula I

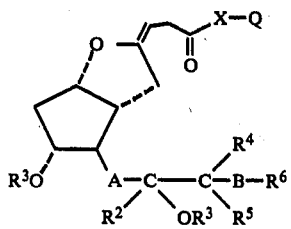

and the analogs thereof wherein the substituents have the following meaning:

Q is a —COOR$^1$, —CH$^2$—OH, —COL$^1$ group wherein
R$^1$ stands for hydrogen, a pharmaceutically acceptable cation, a C$_{1-6}$ alkyl group, C$_{3-10}$ cycloalkyl group, aralkyl or aryl group,
L$^1$ represents an amino group, an alkyl-amino group or a dialkyl-amino group, wherein the alkyl substituents of the amino group are C$_{1-6}$ alkyl,
X is a —CH$_2$—CH$_2$—, —CH=CH—, —CH$_2$—C(CH$_3$)$_2$—, —(CH$_3$)$_2$C—CH$_2$— or a cyclopropylene group,
A stands for a trans- or cis—CH=CH—, —C≡C—, or a —CH$_2$—CH$_2$—group,
R$^2$ represents hydrogen with α- or β-configuration, a methyl or ethyl group,
R$^3$ is hydrogen, a C$_{1-4}$ alkanoyl-, optionally substituted aroyl- or tri-(C$_{1-4}$)alkyl-silyl-protective group,
R$^4$ and R$^5$ stand independently from each other for hydrogen or a C$_{1-4}$ alkyl group,
B represents a methylene group, oxygen or a —N-H—group,
R$^6$ is a C$_{1-6}$ straight or branched alkyl group, an aryl group, a substituted aryl group or a substituted heteroaryl group.

The compounds of the formula I forming the subject matter of the invention can be considered the analogs of the metabolite of the biologically extraordinarily active arachidonic acid, the stable and efficient analog PGI₂ exerting a stronger aggregation inhibiting and vasodilator effect than all materials known so far. PGI₂ prevents the aggregation of blood plaques and dissolves thrombuses already aggregated, respectively, even in nanogram quantities. Due to this unique pharmaceutical effect it can be an extraordinarily valuable medicament for the medical treatment of the disease of this century, of the circulatory diseases, especially thrombosis. So far numerous publications were issued about the clinical use of the substance.

The greatest problem of the use of PGI₂ as a pharmaceutical product is the extraordinary instability of the material; in an acidic or neutral medium it decomposes to 6-oxo-PGF$_{1α}$ equilibrating with the hemiketal immediately. PGI₂ contains the structural unit of a reactive enolether which immediately reacts with an outer proton source or a proton source within the molecule. Thus PGI₂ cannot exist in form of a free acid and the salts and esters thereof are used in pharmaceutical and clinical experiments.

Up to now numerous attempts have been carried out in order to stabilize the enolether structure. Among the stabilized analogs the 7-oxo-PGI₂ and the analogues thereof must be emphasized (European patent application No. 0,031,426 published on July 8, 1981). These are novel, stable PGI₂ analogs possessing excellent pharmaceutical properties. Due to the inductive and conjugative effect of the insertion of the oxo group into position C-7 the eletron density of the enolether and its nucleophility are decreased; thus the stability of the molecule is increased.

The demand for stable prostacyclin analogs could not be satisfied by the analogs until now from every point of view. The increasing stability is accompanied either by a decrease of the effect of the molecule or a deterioration of the selectivity or both. The aim was to prepare such analogs which are free of the deficiencies of the known analogs. Surprisingly it has been found that the 4-oxo-PGI₂ analogs of the formula I of the invention besides that they possess the stability desired for the practical applicability do not show the disadvantageous properties of the earlier analogs.

In the 4-oxo-PGI₂ derivatives of the present invention the oxo group in position C-4 reduces the reactivity of the enolether and increases the stability of the molecule. In acidic and neutral medium the 4-oxo-PGI₂ and the derivatives thereof show surprising stability—they can be maintained in a medium containing 1 N hydrochloric acid and acetic acid for some hours without considerable decomposition—because their decomposition products, the 6-hydroxy-4-oxo-PGI$_1$ and the derivatives thereof (containing a β-hydroxy-ketone structural unit) are reversed to the original 4-oxo-PGI₂ form and the balance shifts in favor of the latter. The 4-oxo-PGI₂ and the analogs thereof can be isolated and maintained in form of a free acid, too, thus the 4-oxo PGI₂ and the derivatives thereof can be considered the most stable 9(O)-PGI₂ analogs in the acidic medium.

The 4-oxo-PGI₂ of the formula I as well as the analogs thereof and the derivatives thereof inhibit the blood plague aggregation caused by the arachidonic acid or ADP or collagen, they affect the circulation, the unstriped muscles, as novel effect they exert a cytoprotective effect, act on the muscular system of the bronchi and on the gastrointestine system and exert numerous other valuable pharmaceutical effects.

The compounds of the formula I as stable prostacyclin analogs inhibited the aggregation caused by 1×10⁻⁶ mole/ml of ADP in blood plaques isolated from human blood on thick plasma measured with the method of Born in a concentration of 15-200 ng/ml(IC$_{50}$) which corresponds to a 1/10-1/100 PGI₂ effect.

These novel prostacyclin analogs exert a strong vasodilator effect similarly to the prostacyclin. On the basis of the haemodynamic parameters of cats narcotized by pentobarbitural the strength of the effect is 1/10-1/100 of the effect of PGI₂. With narcotized dogs a fall of 10-15% is caused in the aortic blood-pressure by an infusion of 1-10 gamma/kg/minute.

The compounds of formula I decrease the tonus of isolated calf coronary artery; in a tenfold dose they exert an effect identical with that of the prostacyclin. The compounds relax the guinea-pig trachea and the human isolated bronchi preparation, the strength of the effect amounts to 1/25 of that one of PGI₂. Furthermore they act on the gastrointestine system, and inhibit the secretion of gastric acid.

As novel prostacyclin analogs the compounds of formula I can be used in human and veterinary therapeutics for the prevention and treatment of different diseases.

a. The administration of these compounds reduces the adhesive character of the blood plagues, inhibits the formation of thrombuses and dissolves thrombuses already formed. Thus they are suitable for the prevention and treatment of the myocardial infarction, post-operative thrombosis and arteriosclerotic diseases. They can be used on the territory of the extracorporal circulation themselves or combined with heparine. They can be used orally, in the form of tablets or capsules, and in the form of intravenous and intramuscular injections or infusions. Their daily dose amounts to 0.05–50 mg/kg of body-weight depending on the form of administration, the gravity of the disease and the age.

b. Inhibition of gastric acid secretion

When used in human and veterinary therapeutics these novel prostacyclin analogs reduce the secretion of gastric acid and thus they are suitable for the prevention and treatment, respectively, of gastric ulcer. They are administered intravenously, intramuscularly or in form of a subcutaneous infusion in a dose of 0.1–20 gamma/kg/minute. When administered orally their dose is 1–10 mg/kg of body-weight per day.

c. Bronchus dilatation

These novel prostacyclin analogues are suitable for the treatment of asthma. They are administered in form of tablets, capsules or spray, the daily dose is 0.01–5 mg/kg of body weight. These products can be combined advantageously with other antiasthmatics, like isoproterenol, ephedrine, xanthine derivatives and corticosteroids.

d. Furthermore they can be used for the treatment of different skin diseases, e.g. psoriasis, different specific and aspecific dermatitises, allergic exanthemas. In this case they are used locally in the form of solutions, inunctions and sprays, the products contain 0.5–2% of the agent.

According to the invention the compounds of formula I are prepared so that a. the compounds of formula III

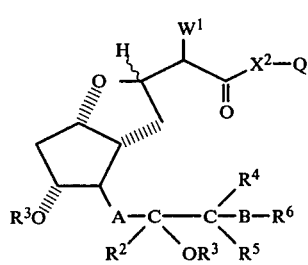

(XIIIX)

wherein Q, $R^1$, $R^2$, $R^3$, $R^4$, $R^5$, $R^6$, A and B are as defined above, $W^1$ stands for an alkyl-thio-, aryl-thio-, substituted aryl-thio- or aryl-seleno group, $X^2$ represents a —CH₂—CH₂—, —CH=CH—, —CH₂—C(CH₃)₂—, —C(CH₃)₂—CH₂—,

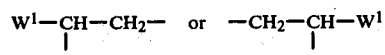

group—are oxidized, then the obtained 5-substituted-4-oxo-PGI₁ derivatives of formula II

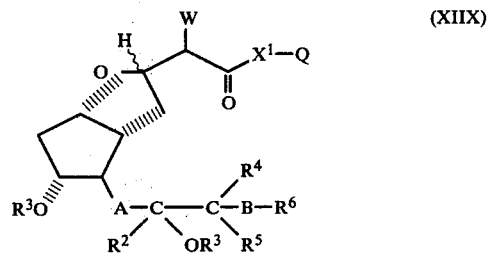

(XIIX)

wherein Q, $R^1$, $R^2$, $R^3$, $R^4$, $R^5$, $R^6$, A and B are as defined above, W stands for an alkyl-sulfinyl-, aryl-sulfinyl group, a substituted aryl-sulfinyl- or aryl-seleninyl group, $X^1$ is a —CH₂—CH₂—, —CH=CH—, —CH₂—C(CH₃)₂—, —C(CH₃)₂—CH₂—,

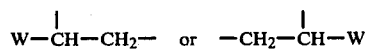

group—are subjected to an elimination reaction to split off of the W-H molecule, or b. the compounds of formula IV

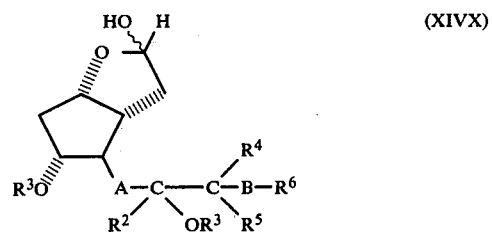

(XIVX)

wherein $R^2$, $R^3$, $R^4$, $R^5$, $R^6$, A and B are as defined above—are reacted in a solvent in the presence of a catalyst with compounds of formula V

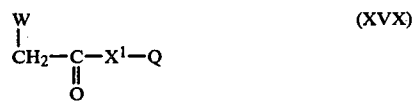

(XVX)

wherein Q, $R^1$, $X^1$ and W are as defined above—then the obtained compounds of formula I are transformed if desired by saponification, hydrolysis, salt formation, or insertion of a protective group to another compound which belongs to the group of compounds of formula I, too.

In order to carry out the elimination reaction of process (a), a thermal reaction or a reaction accomplished in the presence of a base can be used. The temperature of the reaction mixture can vary between 0°–200° C. As solvent aromatic hydrocarbons, benzene, toluene, xylene, halogenated aliphatic and aromatic hydrocarbons, e.g. dichloroethane or chloro-benzene, aprotic dipolar solvents, e.g. dimethyl-formamide, dimethyl-sulfoxide, hexamethylphosphoric acid-triamide, furthermore tertiary organic bases, pyridine, substituted pyridines, trialkyl-amines, 1,5-diazabicyclo[5,4,0]undec-5-en (further: DBU) or 1,5-diazabicyclo[4,3,0]non-5-en (further: DBN) can be used. As base organic and inorganic bases, preferably tertiary aliphatic and aromatic amines, triethyl-amine, pyridine, DBU, DBN, alkali-alkoxides, potassium-carbonate and so on can be used.

The compounds of formula II substituted by sulfinyl or seleninyl in the position of W are prepared from the compounds of formula III which correspond to compounds of formula II containing in
the place of $W^1$
an alkyl-thio-, aryl-thio-,
a substituted aryl-thio- or
a substituted aryl-seleno group,
by the oxidation of the sulfides and the selenides. For the oxidation reaction hydrogen-peroxide, organic peracids, m-chloro-perbenzoic acid, sodium-meta-periodate, further other reagents suitable for the above oxidation can be used (E. Block, Reactions of OrganoSulfur Compounds, Academic Press, Inc. New York, San Francisco, London 1978).

The temperature of the reaction mixture can vary between wide limits: $-78°$ C. to $+50°$ C. As solvent an organic solvent indifferent from the point of view of the reaction, preferably chlorinated aliphatic hydrocarbons and solvents of ether type can be used.

The compounds of formula III can be prepared from bicyclic hemiacetal derivatives of formula IV with 5-substituted-4-oxo-valeric acid derivatives containing an activated methylene group by the one-step Michael addition following the Knoevenagel condensation. If the C-5 substituent of the valeric acid derivatives participating in the Knoevenagel reaction is selected so that it is suitable for an elimination reaction the 4-oxo-PGI$_2$ and the analogs as well as the derivatives thereof can be prepared in one step from the compounds of formula IV.

The compounds of formula IV are known from literature [JACS, 91, 5675 (1969)] and can be prepared in the way described there, respectively.

According to process b/ the compounds of formula IV wherein the substituents are defined as the substituents of the compounds of formula I are reacted with compounds of formula V wherein the substituents are defined as those of the compounds of formula II in a solvent in the presence of a catalyst.

The temperature of the reaction mixture can vary between wide limits: 80° to 200° C. As solvent aromatic and halogenated aromatic hydrocarbons, preferably toluene and xylene are used at a temperature corresponding to the boiling point of the solvent. Furthermore aprotic dipolar solvents, e.g. dimethyl-formamide, hexamethyl-phosphoric acid-triamide can be used. As catalyst of the reactions all known catalyst types of the Knoevenagel reaction, preferably secondary amines—piperidine or morpholine—or the salts thereof formed with organic acids can be applied.

With both methods the prepared compounds of formula I can be isolated to 5(Z) and 5(E) isomers.

In the specification under $C_{1-4}$ alkyl groups the following alkyl groups are to be understood: methyl-, ethyl-, n- and i-propyl, n-, i-, sec- and tert-butyl group. The $C_{1-4}$ alkanoyl groups are those which can be derived from alkanes corresponding to the above $C_{1-4}$ alkyl groups. These are the formyl-, acetyl-, propionyl and butiryl groups. The $C_{1-6}$ alkyl groups include besides the $C_{1-4}$ alkyl groups different pentyl and hexyl groups, too. With an aryl group a phenyl group is meant in the specification. The aryl group can be substituted once or more than once by halogen, a phenyl group, a $C_{1-4}$ alkyl group or a $C_{1-4}$ alkyl group substituted by halogen in any position or it can be unsubstituted. The aralkyl group can be a $C_{1-4}$ alkyl group substituted by the above defined aryl group.

Characteristic representatives of the $C_{3-10}$ cycloalkyl groups are the cyclopropyl-, cyclopentyl-, cyclohexyl-, cycloheptyl-, cyclooctyl-, cyclononyl- and the cyclodecyl groups.

If not indicated otherwise in the specification under a pharmaceutically acceptable cation one equivalent of such positive ions 1, 2 or 3 is to be understood which do not cause undesired side effects in the living organism in doses corresponding to the compounds of the invention. Such cations are first of all the ions of alkali metals, thus the sodium-, potassium and lithium ion, the ions of alkali-earth metals, thus the calcium- and magnesium ion, the aluminium ion, the ammonia ion and the mono- or multivalent ammonia ions which can be derived from different organic amines, e.g. the trishydroxymethyl-ammonia ion.

The alkyl groups of the tri-($C_{1-4}$)alkyl-silyl groups can be identical or different. The heteroaryl group can include one or more heteroatoms, e.g. a nitrogen, oxygen or sulphur atom, in any position of the ring. The substituents of the heteroaryl group can be the ones given at the aryl group.

Further details of the invention are illustrated with the help of the working examples without restricting the invention.

EXAMPLE 1

5-Phenyl-sulfinyl-4-oxo-PGI$_1$-methyl-ester (In formula II W is a phenyl-SO-group, X represents a —CH$_2$—CH$_2$— group, Q stands for a COOR$^1$ group, R$^1$ is a methyl group, A represents a trans-CH=CH— group, R$^2$ is hydrogen with $\beta$-configuration, R$^3$, R$^4$ and R$^5$ are hydrogen, B stands for a methylene group, R$^6$ a propyl group.)

1.60 mg (3.3 mmole) of 5-phenyl-thio-4-oxo-PGI$_1$-methyl-ester (in the compound of formula III W$^1$ is a phenyl-S-group, the other substituents are defined as that one of the named compound) are dissolved in 80 ml of dichloro-methane and under stirring at a temperature of 0° C. 690 mg (3.6 mmole) of 90 percent agent containing m-chloro-perbenzoic acid are added. The reaction takes place within 5 minutes (followed by thin layer chromatography using ethylacetate-acetone in a ratio of 3:1 as eluent). At a temperature of 0° C. 10 ml of 10 percent sodium-hydrogen-sulfite solution are added to the reaction mixture and stirred for 2-3 minutes. Then 250 ml of ethylacetate are added and the mixture is washed successively with 40 ml of water, 40 ml of saturated sodium-hydrogen-carbonate solution, 40 ml of water and finally 30 ml of saturated aqueous sodium-chloride solution. After drying on magnesium-sulfate it is filtered, the solvent is distilled off. By short column chromatography (eluent: ethylacetate-acetone 3:1) 1.60 g (96.8%) of the named compound are obtained in form of a white crystalline substance.

R$_f$: 0.24 eluted with the mixture of ethylacetate-acetone in a ratio of 3:1.

IR (KBr): 1710, 1750 cm$^{-1}$ (C=O).

$^1$H NMR (CDCl$_3$): $\delta$ 7,55 (5H,m, aromatic), 5,5 (2H,m, —CH=CH), 3.5–4.7 (5H,m) 3.60 ppm (3H,s,COOCH$_3$).

EXAMPLE 2

4-Oxo-PGI$_2$-methyl-ester (In formula I the substituents are defined as that of the named compound of Example 1). The 20 ml dimethyl-formamidic solution of 552 mg (1.09 mmole) of 5-phenyl-sulfinyl-4-oxo-PGI$_1$-methyl-ester are heated at a temperature of 145°–150° C. for 2–3 hours. 150 ml of ethylacetate are added to the reaction mixture, then it is washed successively with 3×25 ml of water, 25 ml of saturated aqueous sodium-chloride solution, dried on magnesium-sulfate, filtered, the solvent is distilled off. By short column chromatography on silica gel using the mixture of ethylacetate-acetone in a ratio of 4:1 249 mg (60%) of 4-oxo-5(E)-PGI$_2$-methyl-ester and 37.4 mg (9.0%) of 4-oxo-5(Z)-PGI$_2$-methyl-ester are obtained as compound of the title in form of a colorless crystalline substance. 4-Oxo-5(E)-PGI$_2$-methyl-ester: melting point: 89°–92° C.

R$_f$: 0.37 eluted with the mixture of ethylacetate-acetone in a ratio of 3:1.

$^1$H NMR (CDCl$_3$): δ 5.80 (1H, broad s, C=CH—C=O), 5.6 (2H,m), 4.77 (1H,m), 3.5–4.2 (5H, m, including 3.68 s, COOCH$_3$).

$^1$H NMR (C$_6$D$_6$): δ 5.95 (1H, broad s, C=CH—C=O), 5.5 (2H,m), 4.35 (1H,m), 4.1 (1H,m), 3.7 (1H,m), 3.45 ppm (3H,s, COOCH$_3$).

4-Oxo-5(Z)-PGI$_2$-methyl-ester: R$_f$: 0.25 eluted with a mixture of ethylacetate-acetone in a ratio of 3:1.

$^1$H NMR (C$_6$D$_6$): δ 5.5 (2H,m, —CH=CH—), 5.22 (1H,s,C=CH—C=O), 4.4 (1H,m), 4.15 (1H,m), 3.71 (1H,m) 3.47 (3H,s, COOCH$_3$).

EXAMPLE 3

5-Phenyl-sulfinyl-4-oxo-PGI$_1$-methyl-ester-11,15-diacetate (In formula II R$^3$ is an acetyl group, the other substituents are defined as that of the named compound of Example 1).

110 mg (0.19 mmole) of 5-phenyl-thio-4-oxo-PGI$_1$-methyl-ester-11,15-diacetate/in formula III W$^1$ stands for a phenyl-S-group, R$^3$ represents an acetyl group, the other substituents are defined as that of the named compound) title/are dissolved in 5 ml of dichloro-methane and at a temperature of 0° C. 40.4 mg (0.21 mmole) of m-chloro-perbenzoic acid containing 90% of an agent are added to the solution. The reaction takes place within 5 minutes, then 5 ml of a solution containing 10% of sodium-sulfite are added, the mixture is extracted with 50 ml of ethylacetate. The organic phase is washed successively with 5 ml of water, 5 ml of saturated aqueous sodium-hydrogen-carbonate solution, 5 ml of water, finally with 5 ml of saturated sodium-chloride solution. It is dried on magnesium-sulfate, filtered, the solvent is distilled off. By short column chromatography using the mixture of ethylacetate-hexane in the ratio of 1:1 as eluent 101 mg (89%) of the named compound are obtained in form of a colorless oil.

R$_f$: 0.20 eluted with the mixture of ethylacetate-hexane in the ratio of 1:1.

$^1$H NMR (CDCl$_3$): δ 7.6 (5H,m), 5.5 (2H,m), 3.9–5.3 (5H,m), 3.67 (3H,s), 2.05 (3H,s) 2.00 ppm (3H,s).

EXAMPLE 4

5-Phenyl-sulfinyl-4-oxo-valeric acid-methyl-ester (In formula V W represents a phenyl-SO-group, X is a —CH$_2$—CH$_2$—group, Q stands for a methoxy-carbonyl group).

To the solution containing 20 ml of dichloro-methane of 500 mg (2.1 mmole) of 5-phenyl-thio-4-oxo-valeric acid-methyl-ester at a temperature of 0° C. 443 mg (2.56 mmole) of 90 percent m-chloro-perbenzoic acid are added. The reaction takes place within 5 minutes. Then it is stirred with 5 ml of 10 percent sodium-hydrogen-sulfite solution for 5 minutes, 60 ml of ethylacetate was added and the organic phase is washed successively with 10 ml of water, 10 ml of sodium-hydrogen-carbonate solution, 10 ml of water, 10 ml of saturated aqueous sodium-chloride solution, it is dried on magnesium-sulfate, filtered, the solvent is distilled off. By short column chromatography using the mixture of ethylacetate-hexane in the ratio of 1:1 as eluent 515 mg (96.4%) of the named compound are isolated in form of a white crystalline substance.

Melting point: 50° C. R$_f$: 0.19 eluted with the mixture of ethylacetate-hexane in the ratio of 4:1.

$^1$H NMR (CDCl$_3$): δ 7.4–7.8 (5H,m), 3.92 (2H,s), 3.67 (3H,s), 2.4–2.9 ppm (4H,m).

EXAMPLE 5

4-Oxo-PGI$_2$-methyl-ester 92 mg (0.34 mmole) of 3α,β-hydroxy-6β-(3S-hydroxy-oct-1E-enyl)-7α-hydroxy-2-oxabicyclo[3,3,0]octane are dissolved in 5 ml of xylene, then 260 mg (1.02 mmole) of 5-phenyl-sulfinyl-4-oxo-valeric acid-methyl-ester and 34 μl (0.34 μmole) of piperidine are added. The reaction mixture is heated at 140°–150° C. for 6–8 hours. The crude product is purified by short column chromatography using the solvent mixture of ethylacetate-acetone in the ratio of 4:1 as eluent. Thus 55.1 mg (42%) of 4-oxo-5(E)-PGI$_2$-methyl-ester and 21.4 mg (16.5%) of 4-oxo-5(Z)-PGI$_2$-methyl-ester are isolated. The physical constants thereof are identical with those given in Example 2.

EXAMPLE 6

5-Phenyl-sulfinyl-16,16-dimethyl-4-oxo-PGI$_1$-methyl-ester (In general formula II R$^4$ and R$^5$ stand for a methyl group, the other substituents are defined as that of the compound of the title of Example 1.)

160 mg/0.31 mmole/of 5-phenyl-thio-16,16-dimethyl-4-oxo-PGI$_1$-methyl-ester (in the compound of formula III W$^1$ stands for a phenyl-S-group, R$^4$ and R$^5$ represent a methyl group, the other substituents are defined as that of the named compound) are dissolved in 8 ml of dichloro-methane and at 0° C. 69 mg (0.36 mmole) of m-cloro-perbenzoic acid containing 90% of an agent are added to the solution. After 5 minutes of stirring 1 ml of 10 percent sodium-hydrogen-sulfite solution is added to the reaction mixture and it is stirred at 0° C. for 2–3 minutes. The mixture is diluted with 30 ml of ethylacetate, washed with 5 ml of water, 2×5 ml of saturated aqueous sodium-hydrogen-carbonate solution, 5 ml of water, finally 5 ml of saturated aqueous sodium-chloride solution. It is dried on magnesium-sulfate, the solvent is distilled off. By chromatography on silica gel with ethylacetate 158 mg (95%) of the named compound are obtained in form of a colourless oil.

$R_f$: 0.4 eluted with ethylacetate.

$^1$H NMR (CDCl$_3$): δ 7.48 (5H,m), 5.52 (2H,m), 3.5–4.7 (5H,m), 3.63 (3H,s, COOCH$_3$).

EXAMPLE 7

16,16-Dimethyl-4-oxo-PGI$_2$-methyl-ester 116 mg (0.2 mmole) of 5-phenyl-sulfinyl-16,16-dimethyl-4-oxo-PGI$_1$-methyl-ester are dissolved in 2 ml of dimethyl-formamide and the solution is maintained at 140°–150° C. for 3 hours. The solution is diluted with 20 ml of ethylacetate, then washed with 5 ml of water, 5 ml of saturated aqueous sodium-chloride solution. It is dried on magnesium-sulfate, the solvent is distilled off. By chromatography on 10 g of silica gel with ethylacetate 48 mg (54.5%) of 16,16-dimethyl-4-oxo-5(E)-PGI$_2$-methyl-ester and 13 mg (14.7%) of 16,16-dimethyl-4-oxo-5(Z)-PGI$_2$-methyl-ester are obtained as compounds of the title in form of colorless oils.

16,16-Dimethyl-4-oxo-5(E)-PGI$_2$-methyl-ester: $R_f$: 0.63 eluted with ethylacetate.

$^1$H NMR (CDCl$_3$): δ 5.83 (1H, broad s, C=CH—C=O) 5.58 (2H,m, —CH=CH—) 3.63 ppm (3H,s, COOCH$_3$).

16,16-Dimethyl-4-oxo-5(Z)-PGI$_2$-methyl-ester: $R_f$: 0.48 eluted with ethylacetate.

$^1$H NMR (C$_6$D$_6$): δ 5.5 (2H,m, —CH=CH—), 5.26 (1H,s, C=CH—C=O), 3.49 ppm (3H,s, COOCH$_3$).

EXAMPLE 8

4-Oxo-PGI$_2$-methyl-ester-11,15-diacetate 64 mg (0.1 mmole) of 5-phenyl-sulfinyl-4-oxo-PGI$_1$-methyl-ester-11,15-diacetate (compound of Example 3) are dissolved in 3 ml of dimethyl-formamide and stirred at 110° C. for 10 hours. The solution is diluted with ethylacetate, then washed with water and saturated salt solution, dried on magnesium-sulfate. By short column chromatography using the mixture of ethylacetate-hexane in the ratio of 1:1 39.3 mg (53.8%) of 5(E)-isomer and 8.8 mg (12.0%) of 5(Z)-isomer are obtained as the named compound in the form of a colorless oil.

4-Oxo-5(E)-PGI$_2$-methyl-ester-11,15-diacetate: $R_f$: 0.37 eluted with the mixture of ethylacetate-hexane in the ratio of 1:1.

$^1$H NMR (C$_6$D$_6$): 5.92 (1H,s), 5.3–5.6 (3H,m), 3.46, 1.95 1.97 ppm (3H,s).

4-Oxo-5(Z)-PGI$_2$-methyl-ester-11,15-diacetate: $R_f$: 0.24 eluted with the mixture of ethylacetate-hexane in the ratio 1:1.

$^1$H NMR (C$_6$D$_6$): 5.2–5.6 (4H,m), 2.05 (3H,s), 1.95 ppm (3H,s).

EXAMPLE 9

4-Oxo-5(Z)-PGI$_2$ 190 mg (0.5 mmole) of 4-oxo-5(Z)-PGI$_2$-methyl-ester are dissolved in 2 ml of methanol and after adding 1 ml of 1 N sodium-hydroxide solution the mixture is stirred at room temperature for 5 hours. It is diluted with water, extracted with 3×5 ml of ethylacetate, the pH value of the organic phase is adjusted to 1–2 with sodium-hydrogen-sulfate solution, the mixture is extracted with 3×5 ml of ethylacetate, washed with water, dried on magnesium-sulfate, the solvent is distilled off. Thus 170 mg (92%) of the named compound are obtained in the form of a colorless oil which kept at 0° C. slowly hardens.

$R_f$: 0.17 eluted with the mixture of acetone-ethylacetate in the ratio of 3:1.

EXAMPLE 10

13,14-Didehydro-20-ethyl-4-oxo-PGI$_2$-methyl-ester (In formula I A is an ethinylene group, R$^6$ represents a pentyl group, the other substituents are defined as that of the compound in the title of Example 1.) 300 mg (1 mmole) of 3α,β-hydroxy-6β-(3S-hydroxy-dec-1-inyl)-7α-hydroxy-2-oxabicyclo[3,3,0]octane are dissolved in 15 ml of xylene, then 760 mg (3 mmole) of 5-phenyl-sulfinyl-4-oxo-valeric acid-methyl-ester and 0.1 ml of piperidine are added. By inserting a water separating head-piece the reaction mixture is heated for 6–8 hours. The crude product is purified with the help of short column chromatography using the solvent mixture of ethylacetate-acetone in the ratio of 6:1 as eluent. Thus 220 mg (55%) of 13,14-didehydro-20-ethyl-4-oxo-5(E)-PGI$_2$-methyl-ester and 60 mg (15%) of 13,14-didehydro-20-ethyl-4-oxo-5(Z)-PGI$_2$-methyl-ester are obtained as the compound in the form of a colorless oil.

13,14-Didehydro-20-ethyl-4-oxo-5(E)-PGI$_2$-methyl-ester: $R_f$: 0.46 eluted with the mixture of ethylacetate-acetone in the ratio of 3:1.

$^1$H NMR (C$_6$D$_6$): 5.92 (1H,s, C=CH—C=O), 4.39 (1H,m), 4.13 (1H,m), 3.76 (1H,m), 3.45 (3H,s, COOCH$_3$).

13,14-Didehydro-20-ethyl-4-oxo-5(Z)-PGI$_2$-methyl-ester:

$^1$H NMR (C$_6$D$_6$): 5.24 (1H,s,C=CH—C=O), 4.43 (1H,m), 4.15 (1H,m), 3.8 (1H,m), 3.48 (3H,s, COOCH$_3$).

EXAMPLE 11

2,2-Dimethyl-16-phenoxy-17,18,19,20-tetranor-4-oxo-PGI$_2$-methyl-ester (In general formula I X is a —CH$_2$—C(CH$_3$)$_2$-group, B is oxygen, R$^6$ stands for a phenyl group, the other substituents are defined as that of the named compound of Example 1). 570 mg (2 mmole) of 3α,62-hydroxy-6β-(3S-hydroxy-4-phenoxy-but-1E-enyl)-7α-hydroxy-2-oxabicyclo[3,3,0]octane are dissolved in 25 ml of xylene, then 1.7 g (6 mmole) of 2,2-dimethyl-5-phenyl-sulfinyl-4-oxo-valeric acid-methyl-ester and 0.2 ml of piperidine are added. By inserting a water separating head-piece the reaction mixture is heated for 8 hours. The crude product is purified with the help of short column chromatography using the mixture of ethylacetate-acetone in the ratio of 5:1. Thus 466 mg (55%) of 2,2-dimethyl-16-phenoxy-17,18,19,20-tetranor-4-oxo-5(E)-PGI$_2$-methyl-ester and 150 mg (18%) of 2,2-dimethyl-16-phenoxy-17,18,19,20-tetranor-4-oxo-5(Z)-PGI$_2$-methyl-ester are obtained as the named compound in the form of a colorless oil.

2,2-Dimethyl-16-phenoxy-17,18,19,20-tetranor-4-oxo-5(E)-PGI$_2$-methyl-ester: $R_f$: 0.41 eluted with the mixture of ethylacetate-acetone in the ratio of 4:1.

$^1$H NMR (CDCl$_3$): 5.8 (1H,s,C=CH—C=O), 7.1–7.4 (5H,m,aromatic), 5.6 (2H,m, —CH=CH), 4.7–3.9 (5H,m,CH—O), 3.67 (3H,s,COOCH$_3$).

2,2-Dimethyl-16-phenoxy-17,18,19,20-tetranor-4-oxo-5(Z)-PGI$_2$-methyl-ester: $R_f$: 0.27 eluted with the mixture of ethylacetate-acetone in the ratio of 4:1.

$^1$H NMR (C$_6$D$_6$): 7.1–7.4 (5H,m,aromatic), 5.5 (2H,m, —CH=CH), 5.2 (1H,s,C=CH—C=O), 4.45–3.71 (5H,m,CH—O), 3.45 (3H,s,COOCH$_3$).

EXAMPLE 12

2-Decarboxy-2-hydroxy-methyl-4-oxo-PGI$_2$ (In general formula I Q is a hydroxy-methyl group, the other substituents are defined as that of the compound in the title of Example 1.)

270 mg (1 mmole) of 3α,β-hydroxy-6β-(3S-hydroxy-oct-1E-enyl)-7α-hydroxy-2-oxabicyclo[3,3,0]octane are dissolved in 10 ml of xylene, then 720 mg (3 mmole) of 5-phenyl-sulfinyl-4-oxo-pentanol and 0.1 ml of piperidine are added. The reaction mixture is kept at 140°–150° C. for 6 hours. The crude product is purified by short column chromatography using the solvent mixture of ethylacetate-acetone in the ratio of 3:1 as eluent. Thus 173 mg (52%) of 2-decarboxy-2-hydroxy-methyl-4-oxo-5(E)-PGI$_2$ and 63 mg (18%) of 2-decarboxy-2-hydroxy-methyl-4-oxo-5(Z)-PGI$_2$ are obtained as the named compound in the form of a colorless oil.

2-Decarboxy-2-hydroxy-methyl-4-oxo-5(E)-PGI$_2$:
$R_f$: 0.39 eluted with the mixture of ethylacetate-acetone in the ratio of 3:1.

$^1$H NMR (CDCl$_3$): 5.86 (1H,s,C=CH—C=O), 5.55 (2H,m,—CH=CH—), 4.6–3.7 (5H,m,CH—O), 0.9 (3H,t,—CH$_3$).

2-Decarboxy-2-hydroxy-methyl-4-oxo-5(Z)-PGI$_2$:
$R_f$: 0.27 eluted with the mixture of ethylacetate-acetone in the ratio of 3:1.

$^1$H NMR (C$_6$D$_6$): 5.5 (2H,m,—CH=CH—), 5.18 (1H,s,C=CH—C=O), 4.7–3.7 (5H,m,CH—O), 0.92 (3H,t,—CH$_3$).

The following 4-oxo-PGI$_2$ analogues are prepared from the correspondingly substituted starting materials according to Examples 1 to 12 in form of 5(E)- and 5(Z)-isomers.

20-Methyl-4-oxo-PGI$_2$-methyl-ester.
$R_f$: 5(E): 0.37 5(Z): 0.25 ethylacetate-acetone 3:1.
20-Ethyl-4-oxo-PGI$_2$-methyl-ester.
$R_f$: 5(E): 0.38 5(Z): 0.25 ethylacetate-acetone 3:1.
2,2-Dimethyl-4-oxo-PGI$_2$-methyl-ester.
$R_f$: 5(E): 0.34 5(Z): 0.23 ethylacetate-acetone 3:1.
Δ$^2$-4-Oxo-PGI$_2$-methyl-ester.
$R_f$: 5(E): 0.36 5(Z): 0.23 ethylacetate-acetone 3:1.
16,16-Dimethyl-Δ$^2$-4-oxo-PGI$_2$-methyl-ester.
$R_f$: 5(E): 0.43 5(Z): 0.35 ethylacetate-acetone 2:1.
13,14-Didehydro-Δ$^2$-4-oxo-PGI$_2$-methyl-ester.
$R_f$: 5(E): 0.38 5(Z): 0.24 ethylacetate.
13,14-Didehydro-4-oxo-PGI$_2$-methyl-ester.
$R_f$: 5(E): 0.42 5(Z): 0.30 ethylacetate.
13,14-Didehydro-20-methyl-4-oxo-PGI$_2$-methyl-ester.
$R_f$: 5(E): 0.40 5(Z): 0.30 ethylacetate.
2,2-Dimethyl-13,14-didehydro-4-oxo-PGI$_2$-methyl-ester.
$R_f$: 5(E): 0.38 5(Z): 0.28 ethylacetate.
16-Phenoxy-17,18,19,20-tetranor-4-oxo-PGI$_2$-methyl-ester.
$R_f$: 5(E): 0.53 5(Z): 0.46 ethylacetate-acetone 1:1.
16-(m-Chloro-phenoxy)-17,18,19,20-tetranor-4-oxo-PGI$_2$-methyl-ester.
$R_f$: 5(E): 0.53 5(Z): 0.45 ethylacetate-acetone 1:1.
16-(m-Trifluoro-methyl-phenoxy)-17,18,19,20-tetranor-4-oxo-PGI$_2$-methyl-ester.
$R_f$: 5(E): 0.58 5(Z): 0.46 ethylacetate-acetone 1:1.
15-Epi-4-oxo-PGI$_2$-methyl-ester.
$R_f$: 5(E): 0.37 5(Z): 0.26 ethylacetate.
15-Epi-13,14-didehydro-4-oxo-PGI$_2$-methyl-ester.
$R_f$: 5(E): 0.40 5(Z): 0.30 ethylacetate.
15-Epi-16-phenoxy-17,18,19,20-tetranor-4-oxo-PGI$_2$-methyl-ester.
$R_f$: 5(E): 0.53 5(Z): 0.46 ethylacetate-acetone 1:1.
15-Epi-Δ$^2$-4-oxo-PGI$_2$-methyl-ester.
$R_f$: 5(E): 0.38 5(Z): 0.24 ethylacetate-acetone 3:1.
15-Epi-2,2-dimethyl-4-oxo-PGI$_2$-methyl-ester.
$R_f$: 5(E): 0.36 5(Z): 0.23 ethylacetate-acetone 3:1.
15-Epi-20-methyl-4-oxo-PGI$_2$-methyl-ester.
$R_f$: 5(E): 0.36 5(Z): 0.26 ethylacetate-acetone 3:1.
15-Epi-20-ethyl-4-oxo-PGI$_2$-methyl-ester.
$R_f$: 5(E): 0.38 5(Z): 0.25 ethylacetate-acetone 3:1.
15-Epi-13,14-didehydro-20-ethyl-4-oxo-PGI$_2$-methyl-ester.
$R_f$: 5(E): 0.40 5(Z): 0.31 ethylacetate.

Furthermore from the above compounds by hydrolysis acids and salts and from the latter acid amides are prepared. By the reduction of the acids 2-decarboxy-2-hydroxy-methyl-derivatives can be obtained.

The $R_f$-values indicated in the specification were determined on a MERCK Kieselgel 60 F$_{254}$ plate.

The compounds of formula III used as starting materials in process (a) can be prepared similarly to 5-phenyl-thio-4-oxo-PGI$_1$-methyl-ester the preparation of which is described in the following.

5-Phenyl-thio-4-oxo-PGI$_1$-methyl-ester (In general formula III W$^1$ is a C$_6$H$_5$-S-group, the other substituents are defined as that of the compound in the title of Example 1.)

The reaction mixture containing 920 mg (3.4 mmole) of 3α,β-hydroxy-6β-(3S-hydroxy-oct-1E-enyl)-7α-hydroxy-2-oxabicyclo[3,3,0]octane, 1.64 g (6.88 mmole) of 5-phenyl-sulfenyl-4-oxo-valeric acid-methyl-ester, 5 ml benzene and 7 ml of 0.5 molar piperidinium-acetate solution including benzene is heated for 60 hours using a water separating head-piece. After the reaction (following with thin layer chromatography) 100 ml of ethylacetate are added to the mixture, it is washed with 2×10 ml of water, 10 ml of saturated aqueous sodium-chloride solution, dried on magnesium-sulfate, then the solvent is distilled off. The crude product is submitted to chromatography on 30 g of silicagel at an overpressure of 1.5 bar using ethylacetate as eluent. Thus 1.4 g (84%) of the compound named are obtained in form of a colourless oil. $R_f$: 0.46 eluted with the mixture of ethylacetate-acetone in the ratio of 1:1

IR (film): 1750, 1710 cm$^{-1}$ (C=O).

$^1$H NMR (CDCl$_3$): δ7.4–7.6 (3H,m, aromatic) 7.0–7.2 (2H,m, aromatic) 5.6–5.7 (2H,m,—CH=CH—) 3.4–4.6 (7H, 2H exchangeable for D$_2$O) 3.45 ppm (3H,s, COOH$_3$).

We claim:

1. A compound of formula I

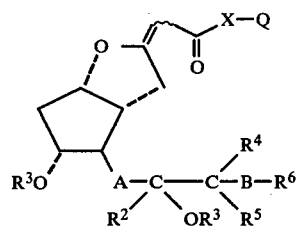

wherein
Q is a —COOR$^1$, —CH$_2$—OH, —CO—L$^1$ group, $R^1$ is hydrogen, a pharmaceutically acceptable cation, $C_{1-6}$ alkyl, $C_{3-10}$ cycloalkyl, phenyl-$C_{1-4}$-alkyl which can be substituted on the phenyl moiety by phenyl, halogen, $C_{1-4}$-alkyl or halogen-substituted-$C_{1-4}$ alkyl, or $R^1$ is phenyl or phenyl substituted by halogen, phenyl, $C_{1-4}$ alkyl or halogen-substituted-$C_{1-4}$ alkyl, $L^1$ represents an amino group or an alkylamino or dialkylamino group containing $C_{1-6}$ alkyl groups, X is a —$CH_2$—$CH_2$—, —CH=CH—, —$CH_2$—$C(CH_3)_2$—, —$(CH_3)_2C$—$CH_2$— or a cyclopropylene group, A is a trans- or cis—CH=CH—, —C≡C— or a —$CH_2$—$CH_2$— group, $R^2$ represents hydrogen with α- or β-configuration, a methyl or ethyl group, $R^3$ is hydrogen, $C_{1-4}$ alkanoyl-, benzoyl or benzoyl whose phenyl group is substituted by halogen, phenyl, $C_{1-4}$ alkyl or halogen-substituted-$C_{1-4}$ alkyl, or tri-$(C_{1-4})$-alkyl-silyl group, $R^4$, $R^5$ stand independently from each other for hydrogen or a $C_{1-4}$ alkyl group, B represents a methylene group, oxygen or a —NH-group and $R^6$ is a $C_{1-6}$ straight or branched alkyl group, phenyl or phenyl substituted by halogen, phenyl, $C_{1-4}$ alkyl or halogen-substituted-$C_{1-4}$ alkyl.

2. 4-Oxo-PGI$_2$-methyl-ester as defined in claim 1.
3. 4-Oxo-16,16-dimethyl-PGI$_2$-methyl-ester as defined in claim 1.
4. 4-Oxo-PGI$_2$-methyl-ester-11,15-diacetate as defined in claim 1.
5. 4-Oxo-5Z-PGI$_2$ as defined in claim 1.
6. 4-Oxo-13,14-didehydro-20-ethyl-PGI$_2$-methyl-ester as defined in claim 1.
7. 2,2-Dimethyl-4-oxo-16-phenyl-17,18,19,20-tetranor-PGI$_2$-methyl-ester as defined in claim 1.
8. 2-Decarboxy-2-hydroxy-methyl-4-oxo-PGI$_2$ as defined in claim 1.
9. 4-Oxo-20-methyl-PGI$_2$-methyl-ester as defined in claim 1.
10. 4-Oxo-20-ethyl-PGI$_2$-methyl-ester as defined in claim 1.
11. 2,2-Dimethyl-4-oxo-PGI$_2$-methyl-ester as defined in claim 1.
12. Δ$^2$-4-Oxo-PGI$_2$-methyl-ester as defined in claim 1.
13. Δ$^2$-4-Oxo-16,16-dimethyl-PGI$_2$-methyl-ester as defined in claim 1.
14. Δ$^2$-13,14-didehydro-4-oxo-PGI$_2$-as methyl-ester as defined in claim 1.
15. 4-Oxo-13,14-didehydro-PGI$_2$-methyl-ester as defined in claim 1.
16. 4-Oxo-13,14-didehydro-20-methyl-PGI$_2$-methyl-ester as defined in claim 1.
17. 2,2-Dimethyl-4-oxo-13,14-didehydro-PGI$_2$-methyl-ester as defined in claim 1.
18. 4-Oxo-16-phenoxy-17,18,19,20-tetranor-PGI$_2$-methyl-ester as defined in claim 1.
19. 4-Oxo-16-(m-chloro-phenoxy)-17,18,19,20-tetranor-PGI$_2$-methyl-ester as defined in claim 1.
20. 4-Oxo-16-(m-trifluoro-methyl-phenoxy)-17,18,19,20-tetranor-PGI$_2$-methyl-ester as defined in claim 1.
21. 15-Epi-4-oxo-PGI$_2$-methyl-ester as defined in claim 1.
22. 15-Epi-4-oxo-13,14-didehydro-PGI$_2$-methyl-ester as defined in claim 1.

23. 15-Epi-4-oxo-16-phenoxy-17,18,19,20-tetranor-PGI$_2$-methyl-ester as defined in claim 1.
24. 15-Epi-Δ$^2$-4-oxo-PGI$_2$-methyl-ester as defined in claim 1.
25. 15-Epi-2,2-dimethyl-4-oxo-PGI$_2$-methyl-ester as defined in claim 1.
26. 15-Epi-4-oxo-20-methyl-PGI$_2$-methyl-ester as defined in claim 1.
27. 15-Epi-4-oxo-20-ethyl-PGI$_2$-methyl-ester as defined in claim 1.
28. 15-Epi-4-oxo-13,14-didehydro-20-ethyl-PGI$_2$-methyl-ester as defined in claim 1.
29. A pharmaceutical composition for inhibiting the aggregation of blood plaques, dilating the bronchi and inhibiting the secretion of gastric acid, which comprises a pharmaceutically effective amount of at least one compound of the formula I as defined in claim 1 in combination with a pharmaceutically acceptable inert carrier.

30. A process for the preparation of 4-oxo-PGI$_2$-derivative of formula I

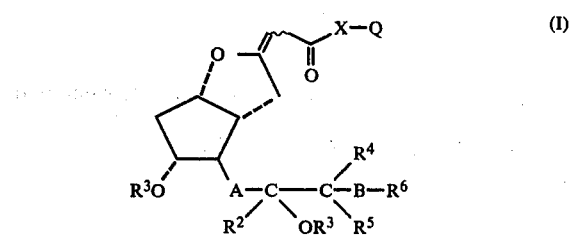

wherein

Q is a —COOR$^1$, —CH$_2$—OH, —CO—L$^1$ group, $R^1$ stands for hydrogen, a pharmaceutically acceptable cation, a $C_{1-6}$ alkyl group, $C_{3-10}$ cycloalkyl-, aralkyl- or aryl group, $L^1$ represents an amino group or an alkylamino or dialkylamino group containing $C_{1-6}$ alkyl groups, X is a —$CH_2$—$CH_2$—, —CH=CH—, —$CH_2$—$C(CH_3)_2$—, —$(CH_3)_2$—$CH_2$— or a cyclopropylene group, A stands for a trans- or cis—CH=CH—, —C≡C— or a —$CH_2$—$CH_2$—group, $R^2$ represents hydrogen with α- or β-configuration, a methyl or ethyl group, $R^3$ is hydrogen, a $C_{1-4}$ alkanoyl, optionally substituted aroyl- or tri-$(C_{1-4})$alkyl-silyl group, $R^4$ and $R^5$ independently from each other for hydrogen or a $C_{1-4}$ alkyl group, B represents a methylene group, oxygen or a —NH—group and $R^6$ is a $C_{1-6}$ straight or branched alkyl group, an aryl group or a substituted aryl group or a substituted heteroaryl group, characterized in that (a) a compound of formula III

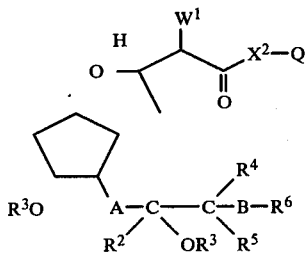

(III)

wherein W¹ stands for an alkyl-thio-, aryl-thio-, substituted aryl-thio- or aryl-seleno group, X² represents a —CH₂—CH₂—, —CH=CH—, —CH₂—C(CH₃)₂—, —C(CH₃)₂—CH₂—,

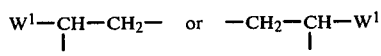

group is oxidized, then the obtained 5-substituted-4-oxo-PGI₁ derivative of formula II

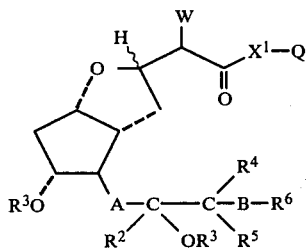

(II)

wherein W stands for an alkyl-sulfinyl-, aryl-sulfinyl-, a substituted aryl-sulfinyl- or aryl-seleninyl group, X¹ is —CH₂—CH₂—, —CH=CH—, —CH₂—CH(CH₃)₂—, —(CH₃)₂C—C₂—,

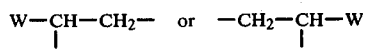

group, is subjected to an elimination reaction to split off a W-H molecule, or (b) a compound of formula IV

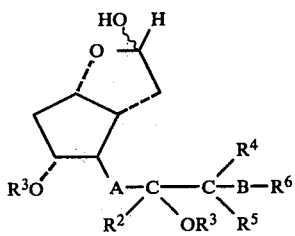

(IV)

is reacted in a solvent in the presence of a catalyst with a compound of formula V

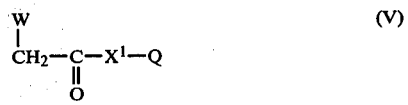

(V)

then the obtained compound of the formula I is transformed if desired by saponification, hydrolysis, salt formation, insertion of a protection group to another compound of the formula I.

31. Process (a) as claimed in claim 30, wherein the oxidation reaction is carried out with an organic or inorganic per-compound in an indifferent solvent at a temperature between −78° C. and +50° C.

32. The process as claimed in claim 31, wherein the per-compound is hydrogen-peroxide, sodium-metaperiodate or m-chloro-perbenzoic acid.

33. The process as claimed in claim 31, wherein the oxidation reaction is carried out in a halogenated aliphatic hydrocarbon or in an ether.

34. Process (a) as claimed in claim 30, wherein the elimination reaction is carried out at a temperature of 80°–200° C. in the presence of aromatic hydrocarbons, halogenated aromatic or aliphatic hydrocarbons, or aprotic polar solvents.

35. The process as claimed in claim 34, wherein the elimination is carried out in benzene, toluene, xylene, dimethyl-formamide, dimethyl-sulfoxide or hexamethyl-phosphoric acid triamide.

36. Process (a) as claimed in claim 30, wherein a compound of formula III, containing an aryl-seleno group in the position of W¹, is oxidized at a temperature between −78° C. and 0° C., then the reaction mixture is warmed to 0°–100° C. and the elimination reaction is carried out.

37. Process (b) as claimed in claim 30, wherein the reaction is carried out at a temperature of 80°–200° C. in the presence of a catalyst applicable in the Knoevenagel condensation, preferably secondary amines, the salts thereof formed with organic acids, using aromatic and halogenated aromatic hydrocarbons or aprotic dipolar solvents.

38. A process as claimed in claim 30 for the preparation of compounds of formula I containing a carboxyl group in the position of Q and of the pharmaceutically acceptable salts thereof, wherein the compound of formula I containing an alkoxycarbonyl- or aryloxycarbonyl group in the position Q is hydrolyzed by a base or an acid, then the compound of formula I obtained in the form of a free acid is transformed to a salt if desired.

39. The process as claimed in claim 30, wherein the compound of formula I obtained in form of a mixture of 5E-5Z isomers is separated to 5E- and 5Z-isomers by chromatography.

* * * * *